US009856153B2

(12) United States Patent
Penhale

(10) Patent No.: US 9,856,153 B2
(45) Date of Patent: Jan. 2, 2018

(54) RADIATION SOURCE ASSEMBLY

(71) Applicant: Trojan Technologies, London (CA)

(72) Inventor: Douglas Penhale, London (CA)

(73) Assignee: Trojan Technologies, London, Ontario (CA)

(*) Notice: Subject to any disclaimer, the term of this patent is extended or adjusted under 35 U.S.C. 154(b) by 0 days.

(21) Appl. No.: 15/302,618

(22) PCT Filed: Apr. 10, 2015

(86) PCT No.: PCT/CA2015/000234
§ 371 (c)(1),
(2) Date: Oct. 7, 2016

(87) PCT Pub. No.: WO2015/154166
PCT Pub. Date: Oct. 15, 2015

(65) Prior Publication Data
US 2017/0022073 A1    Jan. 26, 2017

Related U.S. Application Data

(60) Provisional application No. 61/995,466, filed on Apr. 11, 2014.

(51) Int. Cl.
C02F 1/32      (2006.01)
A61L 2/08      (2006.01)
(Continued)

(52) U.S. Cl.
CPC ............ C02F 1/325 (2013.01); A61L 2/08 (2013.01); H01J 5/60 (2013.01); H01J 61/02 (2013.01);
(Continued)

(58) Field of Classification Search
CPC .... C02F 1/30; C02F 1/32; C02F 1/325; A61L 2/08; A61L 2/10; H01J 5/60; H01J 61/02; H01J 61/36
See application file for complete search history.

(56) References Cited

U.S. PATENT DOCUMENTS 5,030,125 A * 7/1991 Toma ................... H01R 33/975
                                                    313/51
2013/0234037 A1* 9/2013 Moglan ..................... A61L 2/10
                                                    250/432 R
2014/0008547 A1* 1/2014 Strik ....................... C02F 1/325
                                                    250/436

FOREIGN PATENT DOCUMENTS

WO    2012/037644    3/2012
WO    2012/045148    4/2012

OTHER PUBLICATIONS

International Search Report corresponding to International Patent Application No. PCT/CA2015/000234, dated Jul. 22, 2015.
(Continued)

Primary Examiner — David E Smith
(74) Attorney, Agent, or Firm — Michael Stanley Tomsa; McAndrews, Held & Malloy, Ltd.

(57) ABSTRACT

There is disclosed a coupling for a radiation source assembly that comprises an elongate radiation source and an elongate radiation transparent protective sleeve for receiving the elongate radiation source. The coupling disengages in two stages when it is desired to remove the elongate radiation source for servicing (or any other purpose). The coupling is disengaged from a first position in which a seal is made between the sleeve bolt element and the lamp plug element. When this action takes place, the lamp plug element is still secure with respect to the sleeve bolt element but since there is no seal between the two, any fluid which has flooded the elongate radiation source (e.g., due to breakage or other (Continued)

damage to the protective sleeve) will emerge from the coupling warning the operator not to fully disengage the lamp plug element from the sleeve bolt element. If no such fluid is seen by operator, the operator may continue to disengage the lamp plug element from the sleeve bolt element to withdraw the elongate radiation source from the elongate radiation transparent protective sleeve.

21 Claims, 4 Drawing Sheets

(51) Int. Cl.
    *H01J 61/02*     (2006.01)
    *H01J 5/60*     (2006.01)
    *H01J 61/36*     (2006.01)

(52) U.S. Cl.
    CPC ...... *H01J 61/36* (2013.01); *C02F 2201/3227* (2013.01)

(56) References Cited

OTHER PUBLICATIONS

Office Action corresponding to Canadian Application No. 2,944,921, dated Jul. 17, 2017.

\* cited by examiner

RADIATION SOURCE ASSEMBLY

CROSS-REFERENCE TO RELATED APPLICATION

The present application is a National Phase Entry of PCT International Application No. PCT/CA2015/000234, which was filed on Apr. 10, 2015, and claims the benefit under 35 U.S.C. §119(e) of provisional patent application Ser. No. 61/995,466, filed Apr. 11, 2014, the contents of which are hereby incorporated by reference.

BACKGROUND OF THE INVENTION

Field of the Invention

In one of its aspects, the present invention relates to a radiation source assembly. In another of its aspects, the present invention relates to a radiation source module comprising a plurality of radiation source assemblies. Other aspects of the invention will become apparent to those of skill in the art upon reviewing the present specification.

Description of the Prior Art

Fluid treatment systems are known generally in the art.

For example, U.S. Pat. Nos. 4,482,809, 4,872,980 and 5,006,244 [all in the name of Maarschalkerweerd and hereinafter referred to as the Maarschalkerweerd Patents] all describe gravity fed fluid treatment systems which employ ultraviolet (UV) radiation.

Such systems include an array of UV lamp frames which include several UV lamps each of which are mounted within sleeves which extend between and are supported by a pair of legs which are attached to a cross-piece. The so-supported sleeves (containing the UV lamps) are immersed into a fluid to be treated which is then irradiated as required. The amount of radiation to which the fluid is exposed is determined by the proximity of the fluid to the lamps, the output wattage of the lamps and the fluid's flow rate past the lamps. Typically, one or more UV sensors may be employed to monitor the UV output of the lamps and the fluid level is typically controlled, to some extent, downstream of the treatment device by means of level gates or the like.

In recent years, there has been interest in the so-called "transverse-to-flow" fluid treatment systems. In these systems, the radiation source is disposed in the fluid to be treated in a manner such that the longitudinal axis of the radiation source is in a transverse (e.g., substantially orthogonal or vertical orientation of the radiation sources) relationship with respect to the direction of fluid flow past the radiation source. See, for example, any one of:

International Publication Number WO 2004/000735 [Traubenberg et al.];

International Publication Number WO 2008/055344 [Ma et al.];

International Publication Number WO 2008/019490 [Traubenberg et al.];

U.S. Pat. No. 7,408,174 [From et al.];

U.S. Pat. No. 8,395,134 [Penhale et al.]; and

International Publication Number WO 2010/102383 [Penhale et al.].

When it becomes necessary to service the lamp (e.g., to replace it after its service life has been or is about to be exceeded), it is commonly necessary to remove the radiation source assembly from the fluid treatment system and effectively disassemble it to access the various components.

As is known in the art, a significant amount of electrical power is used to operate the lamps in the fluid treatment systems referred to above and it is known those lamps emit large amounts of ultraviolet radiation which is harmful to humans. When it becomes necessary to service the lamp and remove it from the fluid treatment system, it is necessary to disconnect the power supply to the UV lamp. Historically, the prior art has not been focused on safe disconnection of power from the lamp during servicing thereof. Thus, for example, it has been common practise to remove the lamp from the fluid treatment system while it is still connected to the power supply and thereafter to disconnect the power supply from the lamp.

The UV lamps are conventionally housed in a protective quartz sleeve within a housing or chamber filled with water. The water in the housing or chamber is normally pressurized. This pressure applies a force to the closed end of the sleeve. The sleeve is held in position by a sleeve bolt fastened to the water chamber. The sleeve is sealed within the chamber to prevent water from leaking out of the housing or chamber. The lamp and its electrical plug are housed within this quartz sleeve and can be removed without breaking the housing/chamber water seal. A seal on the lamp plug prevents water from entering the sleeve from the external environment or allowing water to leak if the sleeve breaks. The lamp plug is mechanically fastened to the sleeve bolt.

There is always a risk of breakage of the quartz sleeve. Such breakage may occur such that the housing/chamber seal remains intact and water does not leak from the housing/chamber. The seal on the lamp plug is sufficient to prevent water from leaking from the sleeve bolt. If service personnel attempt to remove the lamp and lamp plug from the lamp sleeve, there is a risk that water, together with sleeve and lamp remnants, may be forcibly ejected out of the housing/chamber without warning. This presents a serious injury risk to service personnel.

International Publication Number WO 2012/037644 [Moglan et al. (Moglan)] teaches a radiation source assembly comprising an elongate radiation source; a reactor port for receiving and reversibly securing the elongate radiation source; a top plug element for reversible connection to a proximal end of the radiation source and reversible engagement with the reactor port; the top plug element configured to be disengaged from reactor port without disengagement of the elongate radiation source from the reactor port. In one embodiment, the radiation source assembly comprises a flanged connection bolted to the fluid housing/chamber. A lamp plug is locked into the sleeve bolt with a bayonet style feature. A locking pin is configured to prevent the bayonet feature from rotating accidentally in case of quartz sleeve failure—this is a desirable and important safety feature of the bayonet arrangement taught by Moglan.

While the radiation source assembly taught by Moglan represents an advance in the art, there is room for improvement.

In the arrangement taught by Moglan, the flanged connection and the bayonet feature serve to fix the orientation of the lamp plug. The bayonet connection is the only mechanism capable of holding the lamp plug in position in case of quartz sleeve failure. In addition, embodiments of the bayonet connection illustrated in Moglan necessitate that the lamp plug be twisted or rotated to engage or disengage the electrical connections of the radiation source. Consequently, additional structure and space is needed to engage/disengage the lamp plug and the electrical connections to account for the fact that the lamp plug is being twisted or rotated and the electrical connections of the radiation source are relatively stationary.

It would be desirable to have an arrangement which simplifies the construction (e.g., requires less structure) and requires a small space footprint (important in fluid treatment systems in which the radiation source are packed relatively closely together) while maintaining the safety feature described in Moglan. It would be further desirable to have an arrangement in which two independent mechanisms retain the lamp plug in the sleeve bolt such that either of the mechanisms was capable of retaining the lamp plug in position in case of sleeve failure. It would be further desirable to have an arrangement wherein the connection has a smaller footprint and allows for tighter UV lamp spacing in the multiple UV lamp treatment system. It would be further desirable to have an arrangement wherein the locking mechanism permits the lamp plug to rotate freely to any desirable orientation after installation.

SUMMARY OF THE INVENTION

It is an object of the present invention to obviate or mitigate at least one of the above-mentioned disadvantages of the prior art.

It is another object of the present invention to provide a novel radiation source assembly.

It is another object of the present invention to provide a novel coupling for securing a radiation source assembly to a fluid treatment system.

It is another object of the present invention to provide a novel fluid treatment system.

Accordingly, in one of its aspects, the present invention provides a coupling for a radiation source assembly comprising an elongate radiation source and an elongate radiation transparent protective sleeve for receiving the elongate radiation source, the coupling comprising:

a sleeve bolt element configured to secure the protective sleeve to a fluid treatment housing;

a lamp plug element configured to: (i) be reversibly engageable with respect to the elongate radiation source, and (ii) supply electrical power to the elongate radiation source; and a first seal element configured to be moveable between a first position in which the first seal provides a substantially fluid tight seal between the sleeve bolt element and the lamp plug element and a second position in which the sleeve bolt element and the lamp plug element are unsealed upon non-rotational retraction of the lamp plug element in a direction substantially parallel to a longitudinal axis of the elongate radiation source.

In another of its aspects, the present invention provides a radiation source assembly comprising:

an elongate radiation source;

an elongate radiation transparent protective sleeve for receiving the elongate radiation source;

a sleeve bolt element configured to secure the protective sleeve to a fluid (e.g., water) treatment housing;

a lamp plug element configured to: (i) be reversibly engageable with respect to the elongate radiation source, and (ii) supply electrical power to the elongate radiation source;

a first seal element configured to be moveable between a first position in which the first seal provides a substantially fluid tight seal between the sleeve bolt element and the lamp plug element and a second position in which the sleeve bolt element and the lamp plug element are unsealed upon non-rotational retraction of the lamp plug element in a direction substantially parallel to a longitudinal axis of the elongate radiation source.

The invention also relates to a fluid treatment system incorporating this radiation source assembly.

Thus, the present inventor has developed a coupling for a radiation source assembly that comprises an elongate radiation source and an elongate radiation transparent protective sleeve for receiving the elongate radiation source. The coupling disengages in two stages when it is desired to remove the elongate radiation source for servicing (or any other purpose). The coupling is disengaged from a first position in which a seal is made between the sleeve bolt element and the lamp plug element. When this action takes place, the lamp plug element is still secure with respect to the sleeve bolt element but since there is no seal between the two, any fluid which has flooded the elongate radiation source (e.g., due to breakage or other damage to the protective sleeve) will emerge from the coupling warning the operator not to fully disengage the lamp plug element from the sleeve bolt element. If no such fluid is seen by operator, the operator may continue to disengage the lamp plug element from the sleeve bolt element to withdraw the elongate radiation source from the elongate radiation transparent protective sleeve.

Unlike the bayonet arrangement described above with respect to Moglan, the present coupling and radiation source assembly operates on the basis that the lamp plug element can be disengaged from the sleeve bolt element without the need for any rotation of the lamp plug element. This avoids the requirement for additional structure to create the electrical connection between the lamp plug element and the electrical connectors on the elongate radiation source. This also results in a smaller footprint for construction which facilitates closer packing of radiation source assemblies in the fluid treatment system. These are distinct advantages of the present coupling and radiation source assembly.

Other advantages of the invention will become apparent to those of skill in the art upon reviewing the present specification.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
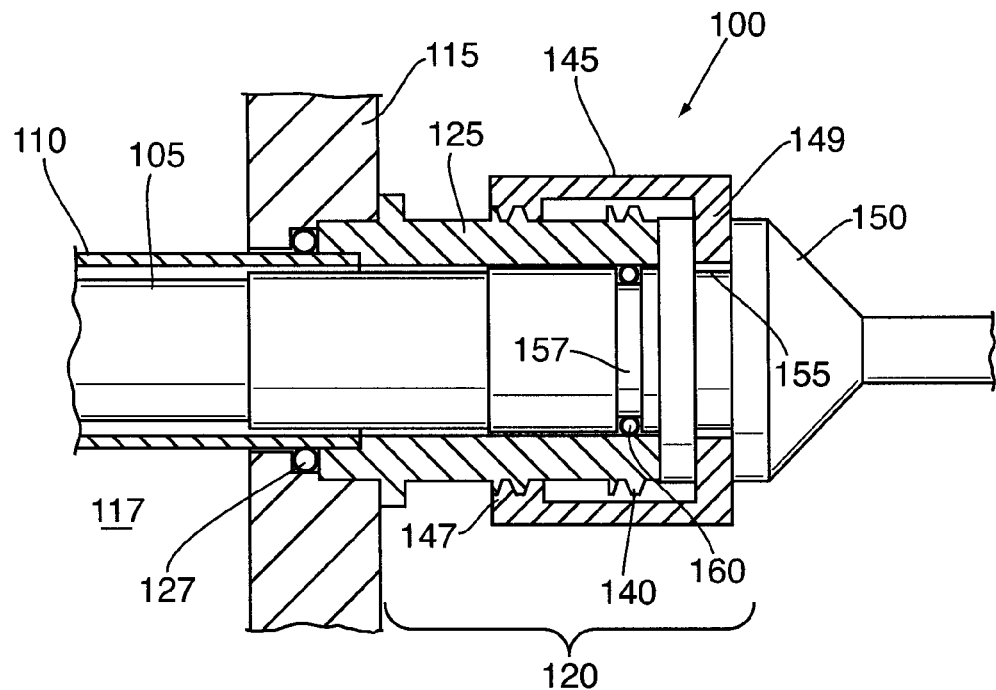
FIGS. 1-4 illustrate various views of a first embodiment of the present radiation source assembly and coupling.
Figure 2:
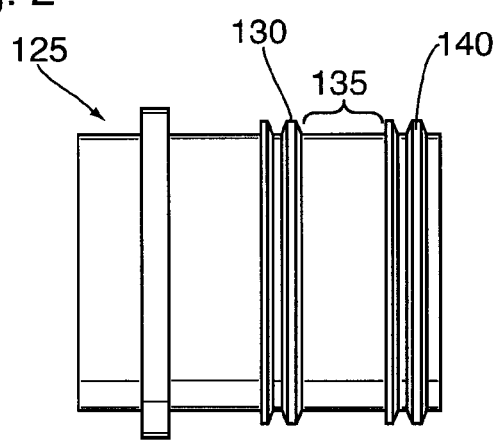

In one of its aspects, the present invention relates to a radiation source assembly comprising: an elongate radiation source; an elongate radiation transparent protective sleeve for receiving the elongate radiation source; a sleeve bolt element configured to secure the protective sleeve to a fluid treatment housing; a lamp plug element configured to: (i) be reversibly engageable with respect to the elongate radiation source, and (ii) supply electrical power to the elongate radiation source; and a first seal element configured to be moveable between a first position in which the first seal provides a substantially fluid tight seal between the sleeve bolt element and the lamp plug element and a second position in which the sleeve bolt element and the lamp plug element are unsealed upon non-rotational retraction of the lamp plug element in a direction substantially parallel to a longitudinal axis of the elongate radiation source.

In another of its aspects, the present invention provides a coupling for a radiation source assembly comprising an elongate radiation source and an elongate radiation transparent protective sleeve for receiving the elongate radiation source, the coupling comprising: a sleeve bolt element configured to secure the protective sleeve to a fluid treatment housing; a lamp plug element configured to: (i) be reversibly engageable with respect to the elongate radiation source, and (ii) supply electrical power to the elongate radiation source; and a first seal element configured to be moveable between a first position in which the first seal provides a substantially fluid tight seal between the sleeve bolt element and the lamp plug element and a second position in which the sleeve bolt element and the lamp plug element are unsealed upon non-rotational retraction of the lamp plug element in a direction substantially parallel to a longitudinal axis of the elongate radiation source.

Preferred embodiments of this radiation source assembly and coupling, respectively, may include any one or a combination of any two or more of any of the following features:
- the radiation source assembly further comprises lamp plug retaining element engaged to the lamp plug element and the sleeve bolt element;
- the lamp plug retaining element is configured to move between a first extended position and a second retracted position;
- in the first extended position the first seal element is in the first position;
- in the second retracted position the first seal element is in the second position;
- in the first extended position the first seal element is in the first position and in the second retracted position the first seal element is in the second position;
- the lamp plug retaining element is in threaded engagement with the sleeve bolt element;
- the sleeve bolt element comprises a first threaded portion and a second threaded portion separated by a space portion, the first threaded portion and the second threaded portion configured to be in threaded engagement with a third threaded portion on the lamp plug retaining element;
- the first seal is configured to be in the first position when the first thread portion of the sleeve bolt element is engaged with the third threaded portion of the lamp plug retaining element;
- the first seal is configured to be in the second position when the third threaded portion of the lamp plug retaining element is in the space portion of the sleeve bolt element;
- the first seal is configured to be in the first position when the first thread portion of the sleeve bolt element is engaged with the third threaded portion of the lamp plug retaining element and the first seal is configured to be in the second position when the third threaded portion of the lamp plug retaining element is in the space portion of the sleeve bolt element;
- the sleeve bolt element comprises a first locking portion configured to secure the lamp plug retaining element in the first extended position;
- the lamp plug retaining element comprises a second locking portion configured to engage the first locking portion in the first extended position;
- the lamp plug retaining element comprises a second locking portion configured to releasably engage the first locking portion in the first extended position;
- at least one of the first locking portion and the second locking portion comprise a biasing element configured to permit the first locking portion and the second locking portion to be engaged to one another;
- at least one of the first locking portion and the second locking portion comprise a biasing element configured to permit the first locking portion and the second locking portion to be disengaged from one another;
- at least one of the first locking portion and the second locking portion comprise a biasing element configured to permit the first locking portion and the second locking portion to be engaged to one another and disengaged from one another;
- the biasing element is comprised in the first locking portion;
- the second locking portion comprises a ridge portion;
- the biasing element is comprised in the second locking portion;
- the first locking portion comprises a ridge portion.
- the biasing element is in an annular configuration;
- the biasing element comprises a ball portion;
- the biasing element comprises a plurality of ball portions optionally coupled to a spring element;
- the sleeve bolt element comprises a first threaded portion and a space portion interposed between the first threaded portion and the first locking portion;
- the first threaded portion is configured to be in engagement with a third threaded portion on the lamp plug retaining element;
- the first threaded portion is configured to be in engagement with a third threaded portion on the lamp plug retaining element when the first seal is in the first position;
- the first threaded portion is configured to be in engagement with a third threaded portion on the lamp plug retaining element when the first seal is in the second position;
- the lamp plug element comprises a first recess portion for engagement with a portion the lamp plug retaining element;
- the first seal element has an annular configuration;
- the first seal element comprises an O-ring sealing element;
- the lamp plug element comprises a second recess portion for receiving the first seal element;
- the elongate radiation transparent protective sleeve comprises a quartz sleeve;
- the elongate radiation transparent protective sleeve comprises a closed end; and/or
- the elongate radiation source comprises an ultraviolet radiation source.

Another aspect of the present invention relates to a fluid treatment system comprising the radiation source assembly described above. Preferred embodiments of either of these fluid treatment systems may include any one or a combination of any two or more of any of the following features:
- the at least one radiation source assembly is oriented such that a longitudinal axis of the elongate radiation source is disposed transverse with respect to the direction of the flow of fluid through the fluid treatment zone;
- the at least one radiation source assembly is oriented such that a longitudinal axis of the elongate radiation source is disposed at an angle with respect to the direction of the flow of fluid through the fluid treatment zone;
- the at least one radiation source assembly is oriented such that a longitudinal axis of the elongate radiation source is disposed orthogonally with respect to the direction of the flow of fluid through the fluid treatment zone;

the at least one radiation source assembly is oriented such that a longitudinal axis of the elongate radiation source is disposed substantially parallel with respect to the direction of the flow of fluid through the fluid treatment zone the fluid treatment zone is configured to receive a pressurized flow of fluid; and/or the fluid treatment zone is configured to receive a pressurized flow of water.

With reference to FIGS. 1-4, there is a illustrated a radiation source assembly 100. Radiation source assembly 100 comprises a radiation source 105 disposed within a protective sleeve 110. This will be apparent to those of ordinary skill in the art. Only a proximal portion of radiation source 105 and protective sleeve 110 is shown for clarity purposes.

Radiation source 105 and protective sleeve 110 are secured to a wall 115 of a fluid treatment system by a coupling 120. As shown, a significant portion of radiation source 105 and protective sleeve 110 is disposed in a fluid treatment zone 117 of the fluid treatment.

Coupling 120 comprises a sleeve bolt element 125, a lamp plug retaining element 145 and a lamp plug element 150.

Sleeve bolt element 125 is secured to wall 115 of the fluid treatment zone by any suitable means (e.g., threaded portion, welding and the like—not shown for clarity). An O-ring 127 is disposed to be in contact with wall 115 of the fluid treatment system, sleeve bolt element 125 and protective sleeve 110 to provide a substantially fluid tight seal to prevent leakage of fluid from fluid treatment zone 117 (e.g., water from a pressurized water treatment zone).

Sleeve bolt element 125 comprises threaded portions 130,140 which are separated by a space portion 135.

Lamp plug retaining element 145 comprises a threaded portion 147 and a proximal portion 149 which is received in a recess 155 in lamp plug element 150.

An O-ring 160 is provided in a recess 157 in lamp plug element 150.

In FIG. 1, it can be seen that radiation source assembly 100 is shown "in use". Thus, O-ring 160 forms a substantially fluid tight seal with an interior surface of sleeve bolt element 125. Threaded portion 130 of sleeve bolt element 125 is engaged with threaded portion 147 of lamp plug retaining element 145. This is the so-called first position of O-ring 160.

When it is desired to access radiation source 105 for servicing (or any other purpose), lamp plug retaining element 145 is rotated to disengage threaded portion 130 of sleeve bolt element 125 from threaded portion 147 of lamp plug retaining element 145. This results in threaded portion 147 of lamp plug retaining element 145 moving into space portion 135 of sleeve bolt element 125—see FIG. 3.

In this configuration O-ring 160 no longer forms a fluid tight seal with the interior surface of sleeve bolt element 125—this is the so-called second position of O-ring 160. In this position, threaded portion 147 of lamp plug retaining element 145 is in space portion 135 of sleeve bolt element 125 and is prevented from further retraction by threaded portion 140 of sleeve bolt element 125.

In this so-called second position of O-ring 160, any fluid (e.g., water from fluid treatment zone 117) that has entered the space between radiation source 105 and protective sleeve 110 (e.g., after breakage of or other damage to protective sleeve 110) will leak out of coupling 120 alerting the operator that there is a danger in further withdrawal of lamp plug element 150. This is particularly the case where fluid treatment zone 117 contains a pressurized flow of fluid (e.g., water). The appearance of any fluid leakage alerts the operator to shut down the fluid treatment system and thereafter remove both radiation source 105 and protective sleeve 110. This is significant safety advantage of the present coupling and radiation source assembly.

Figure 3:
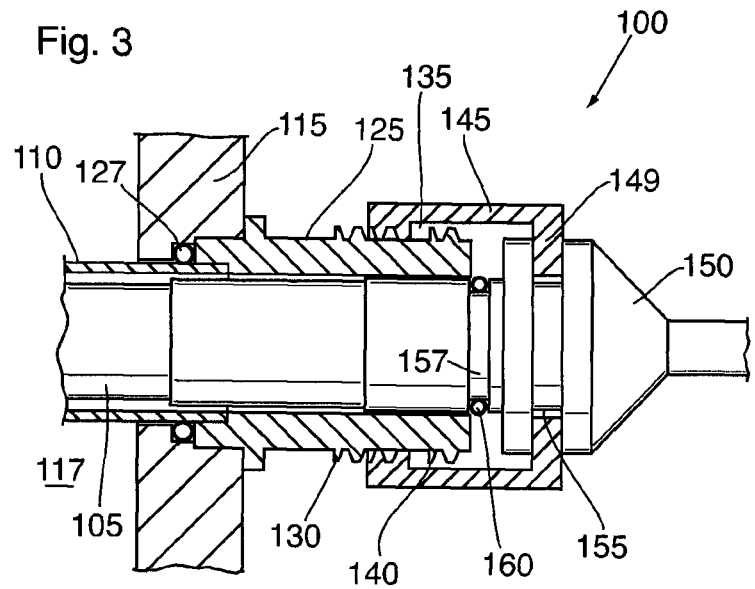
Figure 4:
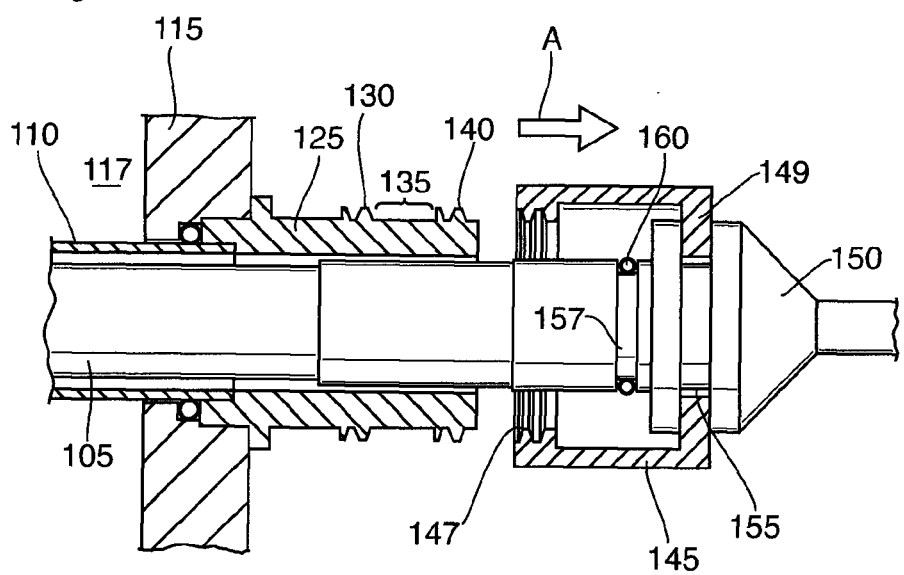

If the operator does not see fluid leakage when coupling 120 is in the position shown in FIG. 3, the operator may continue with disengagement of lamp plug element 150 from sleeve bolt element 125. This may be achieved by turning lamp plug element 145 such that is engages and then disengages from threaded portion 140 on sleeve bolt element 125—see FIG. 4. At this point, it is possible to withdraw radiation source 105 by continuing to retract lamp plug element 150 in the direction of arrow A. This allows for servicing of radiation source 105 while maintaining the fluid treatment system in operation.

With reference to FIGS. 5-8, there is shown a second embodiment of the present radiation source assembly and coupling. In FIGS. 5-8, elements with the same last two numerals are intended to denote similar elements in the embodiment illustrated in FIGS. 1-4.

The principle difference in the embodiment illustrated in FIGS. 5-8 is that threaded portion 130 has been replaced with a ridge portion 230 and lamp plug retaining element 145 has been modified to comprise a locking collar 245a in combination with lamp plug retaining element 245b. An annular arrangement of balls 244 and a helical spring element 248 are disposed between locking collar 245a of lamp plug retaining element 245b.

Figure 5:
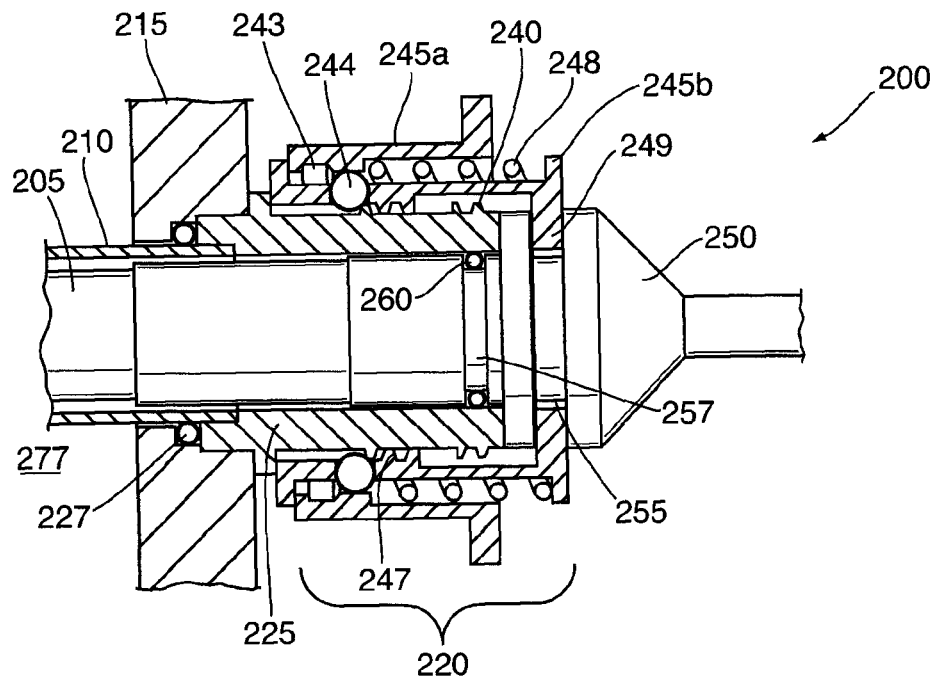
FIGS. 5-8 illustrate a second embodiment of the present radiation source assembly and coupling.
Figure 6:
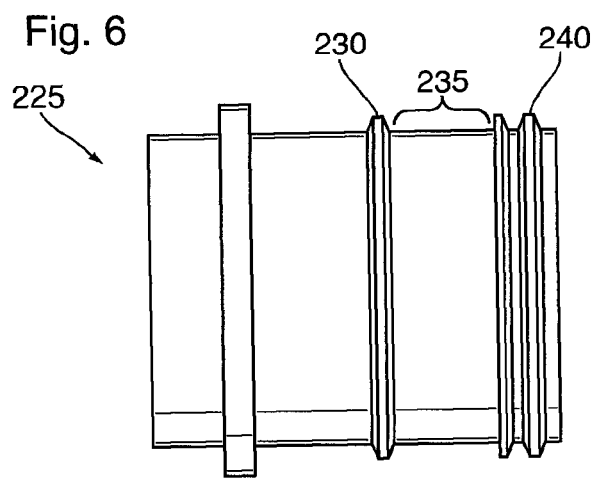
Figure 7:
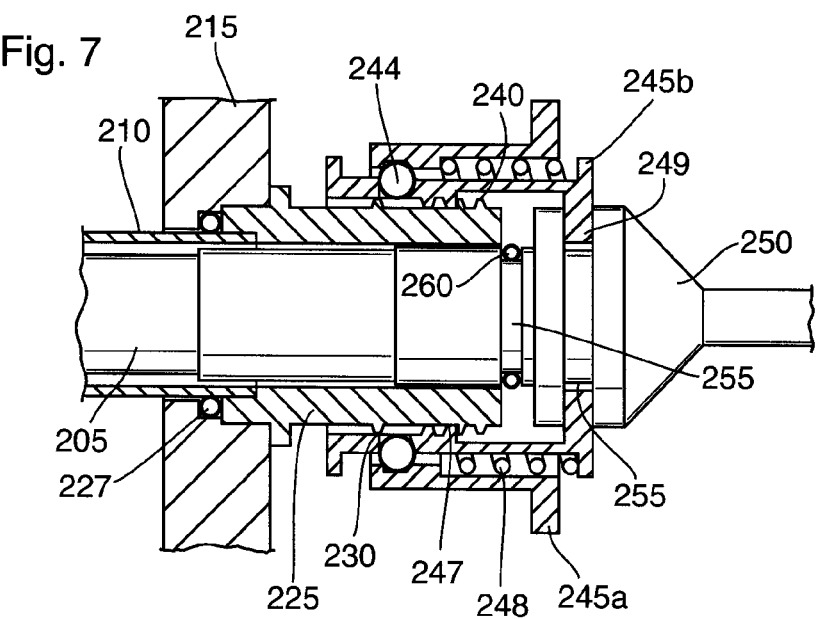

FIG. 5 illustrates coupling 220 when the radiation source assembly is in an "in use" configuration. When it is desired to service or otherwise access radiation source 205, locking collar 245a is retracted toward lamp plug element 250. This action results in balls 244 clearing ridge element 230 such that balls 244 are received in a receptacle or recess 243 in outer locking ring 245a—see FIG. 7. This has the effect of placing O-ring 260 in the so-called second position described above. At this point, the operator will be able to tell if there is fluid leakage from the radiation source assembly due to breakage or other damage to protective sleeve 210.

Figure 8:
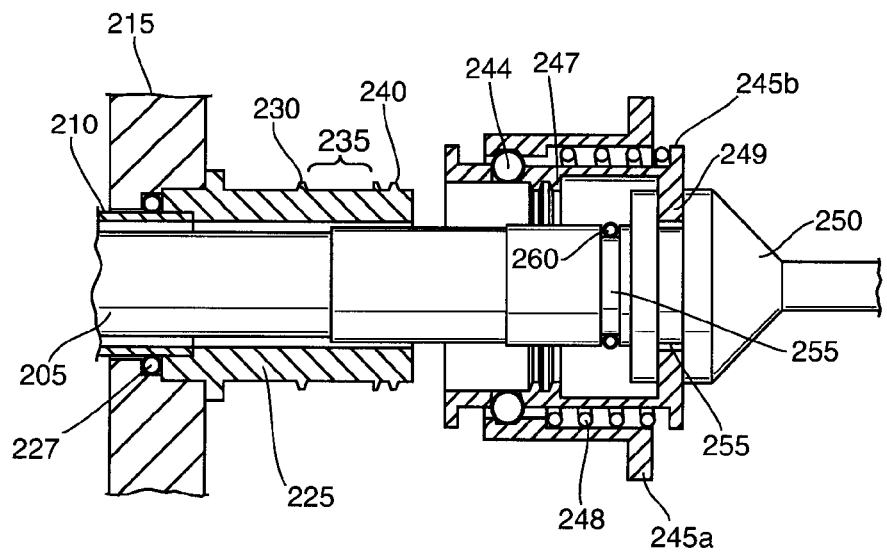

Similar to the embodiment described above, if there is no such leakage of fluid, the operator can continue to disengage lamp plug element 250 by turning lamp plug retaining element 245b such that threaded portion 247 thereof engages and then disengages threaded portion 250 of sleeve bolt element 225—see FIG. 8.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A radiation source assembly comprising:
an elongate radiation source;
an elongate radiation transparent protective sleeve for receiving the elongate radiation source;

a sleeve bolt element configured to secure the elongate radiation transparent protective sleeve to a fluid treatment housing;

a lamp plug element configured to: (i) be reversibly engageable with respect to the elongate radiation source, and (ii) supply electrical power to the elongate radiation source; and a first seal element configured to be moveable between a first position in which the first seal provides a substantially fluid tight seal between the sleeve bolt element and the lamp plug element and a second position in which the sleeve bolt element and the lamp plug element are unsealed upon non-rotational retraction of the lamp plug element in a direction substantially parallel to a longitudinal axis of the elongate radiation source.

2. The radiation source assembly defined in claim 1, further comprising a lamp plug retaining element engaged to the lamp plug element and the sleeve bolt element.

3. The radiation source assembly defined in claim 2, wherein the lamp plug retaining element is configured to move between a first extended position and a second retracted position.

4. The radiation source assembly defined in claim 3, wherein in the first extended position the first seal element is in the first position.

5. The radiation source assembly defined in claim 3, wherein in the second retracted position the first seal element is in the second position.

6. The radiation source assembly defined in claim 3, wherein in the first extended position the first seal element is in the first position and in the second retracted position the first seal element is in the second position.

7. The radiation source assembly defined in claim 3, wherein the sleeve bolt element comprises a first locking portion configured to secure the lamp plug retaining element in the first extended position.

8. The radiation source assembly defined in claim 7, wherein at least one of the first locking portion and the second locking portion comprise a biasing element configured to permit the first locking portion and the second locking portion to be engaged to one another and disengaged from one another.

9. The radiation source assembly defined in claim 8, wherein the biasing element is in an annular configuration.

10. The radiation source assembly defined in claim 2, wherein the lamp plug element comprises a first recess portion for engagement with a portion the lamp plug retaining element.

11. A fluid treatment system comprising a fluid treatment zone configured to receive a flow of fluid and at least one radiation source assembly defined in claim 1, wherein at least a portion of the elongate radiation transparent protective sleeve is disposed in the fluid treatment zone.

12. A coupling for a radiation source assembly comprising an elongate radiation source and an elongate radiation transparent protective sleeve for receiving the elongate radiation source, the coupling comprising:

a sleeve bolt element configured to secure the elongate radiation transparent protective sleeve to a fluid treatment housing;

a lamp plug element configured to: (i) be reversibly engageable with respect to the elongate radiation source, and (ii) supply electrical power to the elongate radiation source; and a first seal element configured to be moveable between a first position in which the first seal provides a substantially fluid tight seal between the sleeve bolt element and the lamp plug element and a second position in which the sleeve bolt element and the lamp plug element are unsealed upon non-rotational retraction of the lamp plug element in a direction substantially parallel to a longitudinal axis of the elongate radiation source.

13. The coupling defined in claim 12, further comprising a lamp plug retaining element engaged to the lamp plug element and the sleeve bolt element.

14. The coupling defined in claim 13, wherein the lamp plug retaining element is configured to move between a first extended position and a second retracted position.

15. The coupling defined in claim 14, wherein in the first extended position the first seal element is in the first position.

16. The coupling defined in claim 14, wherein in the second retracted position the first seal element is in the second position.

17. The coupling defined in claim 14, wherein in the first extended position the first seal element is in the first position and in the second retracted position the first seal element is in the second position.

18. The coupling defined in claim 14, wherein the sleeve bolt element comprises a first locking portion configured to secure the lamp plug retaining element in the first extended position.

19. The coupling defined in claim 18, wherein at least one of the first locking portion and the second locking portion comprise a biasing element configured to permit the first locking portion and the second locking portion to be engaged to one another and disengaged from one another.

20. The coupling defined in claim 19, wherein the biasing element is in an annular configuration.

21. The coupling defined in claim 16, wherein the biasing element comprises a plurality of ball portions optionally coupled to a spring element.

* * * * *